US00PP12495P2

(12) United States Plant Patent
Utecht

(10) Patent No.: US PP12,495 P2
(45) Date of Patent: Mar. 26, 2002

(54) GERANIUM PLANT NAMED 'FISGENTA'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/772,935

(22) Filed: Jan. 31, 2001

(51) Int. Cl.[7] ..... A01H 5/00
(52) U.S. Cl. ..... Plt./329
(58) Field of Search ..... Plt./329, 325, 330

(56) References Cited

U.S. PATENT DOCUMENTS

PP9,748 P * 12/1996 Dümmen ..... Plt./330

OTHER PUBLICATIONS

GTITM UPOVROM Citation for 'Fisgenta' as per QZ PBR 991468; Oct. 20, 1999.*
Fischer–Schmülling Plant Alliance Catalog featuring 'FISGENTA' on p. 11 (2001).
Official Gazette of the Community Plant Variety Office Dec. 15, 1999; European Union Application, denomination, decision for 'FISGENTA'.
German Application for 'FISGENTA' Dec. 15, 1998.
German Proprosed Denomination for 'FISGENTA' Aug. 15, 1999.
Plant Varieties Journal, Jan. 2001, No. 38, pp. 53–54 (Canada).

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisgenta', as described and illustrated, and particularly characterized by the combined features of intense purple-red, semi-double flowers, red eyes on petals, large umbels, well above the foliage, reddish peduncles, dark-green foliage with slight zonation, and medium tall, fairly round plant habit.

1 Drawing Sheet

BACKGROUND OF THE INVENTION

The present invention comprises a new and distinct cultivar of geranium, botanically known as *Pelargonium zonale*, and hereinafter referred to by the cultivar name 'Fisgenta'.

'Fisgenta' is a product of a planned breeding program which had the objective of creating new geranium varieties with red-purple flower color, dark-green foliage, and fair branching ability.

'Fisgenta' originated from a hybridization made by the inventor Angelika Utecht in a controlled breeding program in Galdar, Gran Canaria, Spain, in 1996.

The female parent was a hybrid seedling, No. K94-1960-1 (unpatented), derived from a cross between 'Fisdino' (U.S. Plant Pat. No. 8,761) and seedling No. K92-876-2 (unpatented). The seedling was characterized by single-type, intense purple-pink flowers, dark-green foliage, but poor branching ability. The male parent of 'Fisgenta' was the variety 'HWD Violetta', (U.S. Plant Pat. No. 9,748), having violet-pink, orange-based, semi-double flowers, medium green zoned foliage, and relatively compact, round plant habit.

'Fisgenta' was selected as one flowering plant within the progeny of the stated cross by Angelika Utecht in 1997 in a controlled environment in Galdar, Gran Canaria, Spain. The first act of asexual reproduction of 'Fisgenta' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fisgenta' are firmly fixed and are retained through successive generations of asexual reproduction.

'Fisgenta' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fisgenta' in combination distinguish this geranium as a new and distinct cultivar:

1. Intense purple-red, semi-double flowers;
2. Large inflorescences on reddish peduncles, well above the foliage;
3. Dark-green foliage with weak zonation;
4. Moderately vigorous growth, and medium tall plant habit; and
5. Medium spring flowering response.

Of the many commercial cultivars known to the present inventor, the most similar in comparison to 'Fisgenta' are the varieties 'Fispurple', U.S. Plant patent Ser. No. 09/631,974, 'Fisdino' and the parental variety 'HWD Violetta'.

In comparison to 'Fispurple', 'Fisgenta' has a more bluish tone of flower color, red eyes on the center of the petals, which lack with 'Fispurple', and dark green foliage, in contrast to the medium-green leaves of 'Fispurple'. Furthermore, 'Fisgenta' grows more vigorously and develops a higher foliage canopy than 'Fispurple', which has a low and compact plant habit.

In contrast to 'Fisdino', with medium-green foliage, 'Fisgenta' has dark-green foliage, more round shaped flowers, and somewhat less vigorous growth. In contrast to 'HWD Violetta', 'Fisgenta' has petals with red eyes, and dark-green foliage, while 'HWD Violetta' has medium green leaves.

BRIEF DESCRIPTION OF THE DRAWING

The accompanying photographic drawing shows typical flower and foliage characteristics of 'Fisgenta' with colors being as true as possible with an illustration of this type. The photograph shows a flowering pot plant. The measurements were taken in Langley, British Columbia, Canada, on Jul. 20, 2000, 15 weeks after planting of rooted cuttings into 6 inch pots. The plants had not been pinched. In the following description color references are made to The Royal Horticultural Society Colour Chart (R.H.S.). The color values were determined indoors from plants developed in a greenhouse in May 2000, in Hillscheid, Germany.

Classification:

*Botanical.*—A hybrid of the species *Pelargonium zonale* L'Hérit.

*Commercial.*—Zonal geranium, cv. 'Fisgenta'.

Inflorescence:

*Umbel.*—Shape: Slightly flattened, semi-spherical. Average diameter: 117 mm. Average depth: 55 mm. Peduncle length: 176 mm. Peduncle color: Most often reddish brown, color range RHS 181 A–B; peduncle of young umbel with flower buds is green, RHS 143 B. Pedicel length: 29 mm. Pedicel color: Reddish, RHS 181 A, to dark red, near the upper end, RHS 60 A. Number of flowers per umbel: About 30–40. Lastingness of the umbel: Approximately 18 days at 18° C.

*Corolla.*—Average diameter: 43 mm. Form: Weakly semi-double. Shape: Almost round, open, cup-shaped. Number of petals: 7–8. Petal Size: Upper petals 23–24 mm long, 18–22 mm wide; lower petals 22–24 mm long, 23–25 mm wide. Petal Shape: Oblong to almost obovate, upper end rounded; attenuate base, margin mostly entire with very slight crenation at the tip of the upper petals only. Color (general tonality from a distance of three meters): Magenta (red-purple), with red eyes (not very distinct because of the small difference of colors). Color of upper petals: RHS 66 A. Markings of upper petals: Red eyes, more reddish than RHS 57 A, and orange-red bases, RHS 44 A. Color of lower petals: Color varying between RHS 66 A and RHS 74 A. Markings on lower petals: Small red eyes, more reddish than but closest to RHS 57 A. Color of lower surface of petals: About RHS 66 B. Number of petaloids: 0–1. Color of petaloids: Upper surface, RHS 66 A, lower surface RHS 66 B. Color of sepals: Outer surface green tips, RHS 143 A, dark-red base, closest to RHS 60 A; inner surface green, RHS 143 B, reddish base closest to RHS 47 A. Number of sepals: 5. Sepal size: 12–13 mm long, 4–5 mm wide for the largest upper sepal, 2–3 mm wide for other sepals. Sepal shape: Linear to lanceolate, acute tip, truncate base.

*Bud:* (*just before petals unfold*).—Shape: Elliptical. Sepal Color (lower part): Green, RHS 137 D, red base, RHS 181 A. Petal Color (upper part): Bluish red, coloration varying between RHS 57 A and RHS 66 A. Length: 17 mm. Width: 8 mm.

*Reproductive organs.*—Androecium: 5 fertile anthers, white filaments, yellow-orange pollen, RHS 33 A. Gynoecium: 5–6-lobed dark-red stigma and style, between RHS 46 A–57A, one pistil per flower. Fertility/seed set: Occasionally a few seeds are developed.

*Spring flowering response period.*—In Hillscheid, Germany, in 2000 plant had on average 1.2 flowers opened 9 weeks after planting of rooted cuttings.

*Outdoor flower production.*—Average number of flowers, the flower count in 2000 in Hillscheid, Germany, indicated about 3–4 inflorescences per plant in mid May.

*Durability.*—Good stability of flower color, no shattering good rain resistance.

*Lastingness of the individual bloom.*—Approximately 9 days.

*Fragrance.*—None.

Plant:

*Foliage.*—Form: Kidney-shaped, with open base. Margin: Bicrenated. Apex: Rounded, distinctly wavy. Base: Open, roughly cordate. Size of leaf: 71 mm wide, 45 mm length. Color of upper surface: Dark green, approximately RHS 137 A. Color of lower surface: RHS 137 D. Color of zonation: Weak, brown, about RHS 166 A. Petioles: 5.5–6.5 cm long, color RHS 143 C.

*General appearance and form.*—Stem color: Green, RHS 143 A. Internode length: 10–20 mm. Branching pattern: 4.3 branches. Plant size: 20 cm in height as measured from the soil to the surface of the foliage canopy to 31 cm wide.

Disease/pest resistance/susceptibility: None observed to date.

I claim:

1. A new and distinct cultivar of geranium plant named 'Fisgenta', as described and illustrated.

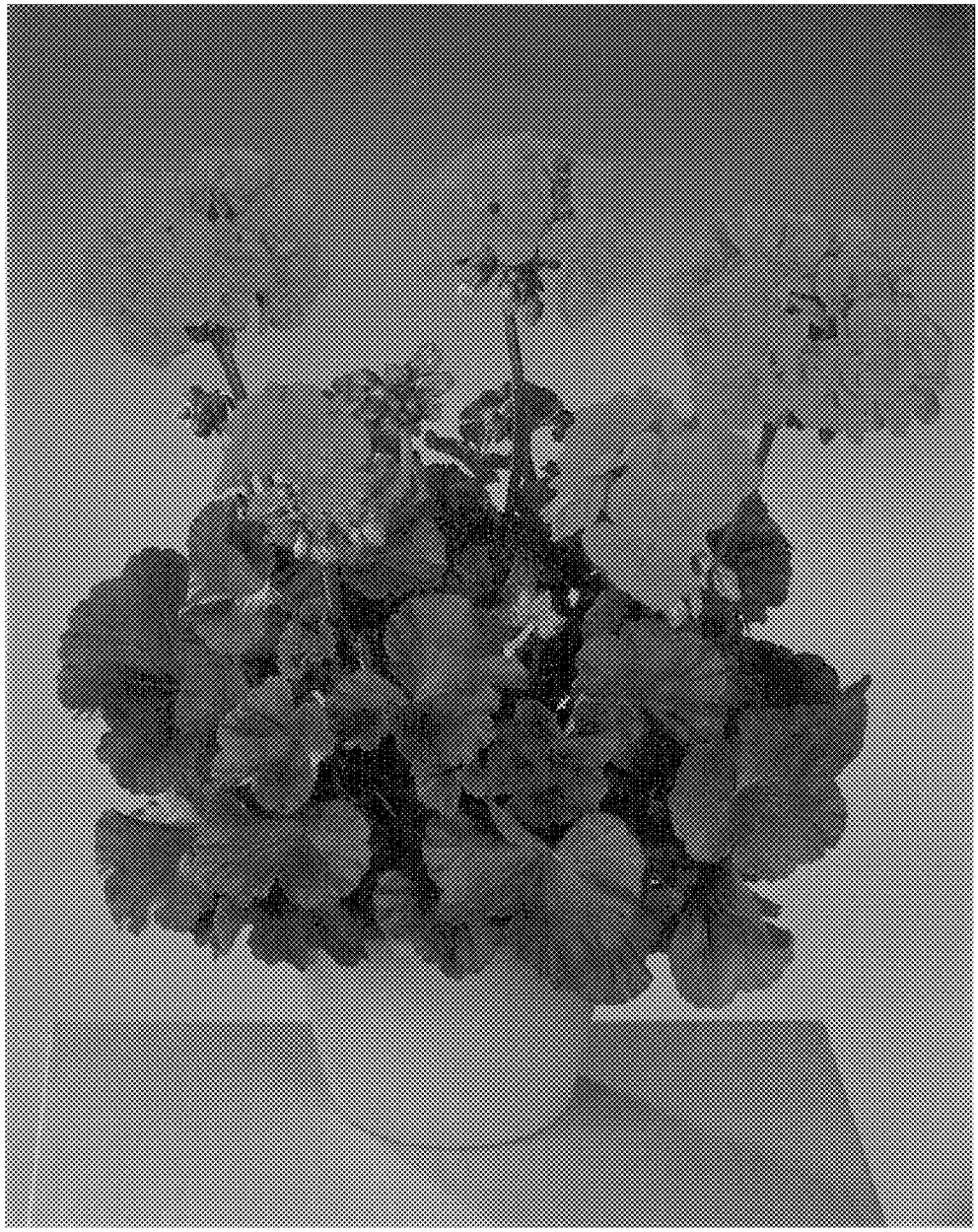

* * * * *